US012653987B2

(12) United States Patent
Boulangé et al.

(10) Patent No.: US 12,653,987 B2
(45) Date of Patent: Jun. 16, 2026

(54) DRIVE MODULE OF ELONGATE FLEXIBLE MEDICAL DEVICE OF CATHETER ROBOT

(71) Applicant: ROBOCATH, Rouen (FR)

(72) Inventors: Marc Boulangé, La Gaillarde (FR); Benoît Hoefler, Rouen (FR)

(73) Assignee: ROBOCATH, Rouen (FR)

( * ) Notice: Subject to any disclaimer, the term of this patent is extended or adjusted under 35 U.S.C. 154(b) by 393 days.

(21) Appl. No.: 18/259,386

(22) PCT Filed: Dec. 22, 2021

(86) PCT No.: PCT/EP2021/087255

§ 371 (c)(1),
(2) Date: Jun. 26, 2023

(87) PCT Pub. No.: WO2022/144267

PCT Pub. Date: Jul. 7, 2022

(65) Prior Publication Data

US 2024/0058583 A1 Feb. 22, 2024

(30) Foreign Application Priority Data

Dec. 29, 2020 (FR) ...................................... 2014222

(51) Int. Cl.
*A61M 25/01* (2006.01)
*A61B 34/30* (2016.01)

(52) U.S. Cl.
CPC ......... *A61M 25/0113* (2013.01); *A61B 34/30* (2016.02); *A61B 2034/301* (2016.02)

(58) Field of Classification Search
CPC ............... A61M 25/0113; A61B 34/30; A61B 2034/301
See application file for complete search history.

(56) References Cited

U.S. PATENT DOCUMENTS 10,695,533 B2 * 6/2020 Deboeuf ................ A61B 34/30
2015/0297864 A1 10/2015 Kokish et al.
(Continued)

FOREIGN PATENT DOCUMENTS

CN 110236680 B 7/2020
EP 3593851 A1 1/2020
(Continued)

OTHER PUBLICATIONS

Office Action, issued in Japanese Patent Application No. 2023-539894 dated Feb. 18, 2025.
(Continued)

*Primary Examiner* — Michelle Lopez
(74) *Attorney, Agent, or Firm* — NIXON & VANDERHYE

(57) ABSTRACT

A drive module for an elongate flexible medical device of a catheter robot includes at least two drive devices respectively carrying two pad holders, each drive device being self-supporting and including three drive units which are independent of each other. At least two drive units have a structure preventing rotational movements of the pad holder. That structure includes a drive crossmember, driven by the drive motor, a pad holder crossmember rigidly connected to the pad holder, driven by the drive crossmember, two connecting rods respectively connected by one of their ends to two pivoting points of the drive crossmember set apart from each other, and by the other end to two pivoting points of the pad holder crossmember set apart from each other. The drive crossmember, the pad holder crossmember, and the two connecting rods form a parallelogram deformable at its vertices which are the four pivoting points.

20 Claims, 7 Drawing Sheets

(56)         References Cited

U.S. PATENT DOCUMENTS

| | | |
|---|---|---|
| 2016/0354582 A1 | 12/2016 | Yu et al. |
| 2017/0151024 A1 | 6/2017 | Deboeuf et al. |
| 2020/0138530 A1* | 5/2020 | Nowatschin ........... A61B 34/30 |
| 2021/0338355 A1* | 11/2021 | Yip ......................... A61B 1/05 |

FOREIGN PATENT DOCUMENTS

| | | |
|---|---|---|
| FR | 1555377 A | 1/1969 |
| FR | 3022147 B1 | 7/2016 |
| JP | 2017064892 A | 4/2017 |
| JP | 2017526397 A | 9/2017 |
| WO | 2015189531 A2 | 12/2015 |
| WO | 2018176457 A1 | 10/2018 |

OTHER PUBLICATIONS

International Search Report for PCT/EP2021/087255 mailed Feb. 25, 2022, 5 pages.
Written Opinion of the ISA for PCT/EP2021/087255 mailed Feb. 25, 2022, 5 pages.

* cited by examiner

DRIVE MODULE OF ELONGATE FLEXIBLE MEDICAL DEVICE OF CATHETER ROBOT

CROSS-REFERENCE TO RELATED APPLICATIONS

This application is the U.S. national phase of International Application No. PCT/EP2021/087255 filed Dec. 22, 2021 which designated the U.S. and claims priority to FR 2014222 filed Dec. 29, 2020, the entire contents of each of which are hereby incorporated by reference.

FIELD OF THE INVENTION

The invention relates to the technical field of drive modules for an elongate flexible medical device of a catheter robot.

TECHNOLOGICAL BACKGROUND OF THE INVENTION

According to the prior art, for example described in patent application FR 1555377, a drive module for an elongate flexible medical device of a catheter robot is known which is precise.

This drive module for an elongate flexible medical device of a catheter robot comprises a motion transmission system comprising a base of a drive member of a movable element, three actuators driving the base of the drive member respectively in three mutually distinct directions of translation, via three respective interfaces with the base of the drive member. The three interfaces are substantially planar, orthogonal to one another, and nested one inside the other.

But while being relatively small in size and weight, this drive module for an elongate flexible medical device of a catheter robot is still too bulky for some applications.

OBJECTS OF THE INVENTION

The object of the present invention is to provide a drive module for an elongate flexible medical device of a catheter robot that at least partially overcomes the above disadvantages.

More particularly, the invention aims to provide a drive module for an elongate flexible medical device of a catheter robot which is suitably miniaturized, and is very precise in the movements of the pad holders bearing the pads that grip and move the elongate flexible medical device(s) inserted into the catheter robot.

To obtain a drive module for an elongate flexible medical device of a catheter robot having this good compromise between miniaturization and precision, the drive module proposed by the invention:

will have a general architecture comprising at least two drive devices, one per pad holder,
each drive device comprising three drive units, one per direction of translation of each pad holder,
and will combine, within this general architecture, several particular structural characteristics, namely:
the self-supporting nature of each drive device,
the independence between the drive units of a same drive device,
a particular structure for preventing parasitic rotations, for at least two drive units per drive device, integrating kinematics of a deformable parallelogram.

To this end, the invention proposes a drive module for an elongate flexible medical device of a catheter robot, comprising: at least two drive devices respectively carrying two pad holders located opposite one another and respectively intended to receive two pads which, as they approach each other, will grip the elongate flexible medical device in order to then drive it in translation and/or in rotation, each drive device being self-supporting and comprising three drive units which are independent of each other, driving the pad holder in translation respectively in the three orthogonal spatial directions, which each comprise their drive motor, and at least two drive units have a rotation-preventing structure for preventing rotational movements of the pad holder: a self-supporting drive device being a drive device in which its own structure ensures that the pad holder is held in position without the presence of an additional support element, a drive unit that is independent of the other drive units being a drive unit which only supports its own weight without also supporting the weight of another drive unit, a rotation-preventing structure comprising: a drive crossmember, driven by the drive motor, a pad holder crossmember, rigidly connected to the pad holder and driven by the drive crossmember, two connecting rods respectively connected: by one of their ends to two pivoting points of the drive crossmember which are set apart from each other, and by the other of their ends to two pivoting points of the pad holder crossmember which are set apart from each other, the drive crossmember, the pad holder crossmember, and the two connecting rods together forming a parallelogram that is deformable at its four vertices which are said four pivoting points.

According to some embodiments of the invention, the proposed drive module, in addition to being miniaturized, reduces the number of moving components in order to reduce inertia and improve the responsiveness of the catheter robot.

According to some embodiments of the invention, the drive device for the self-supporting pad holder supports the pad holder by itself, and by itself ensures that the pad holder is held in position. The pad holder retains its position when the drive device is switched off. The pad holder remains motionless; it is not wobbly. The drive device thus does not require any additional support element intended to support the pad holder.

According to some embodiments of the invention, the independent kinematic units are not mounted on top of each other; indeed, each kinematic unit only supports its own weight. Each drive device for a pad holder comprises three kinematic units, one kinematic unit for each axis of the three translational movements that the pad holder can perform. The pad holder will be able to perform pure translational movements along each of the three spatial axes. Each kinematic unit has the function of moving the pad holder along one of these three axes.

According to some embodiments of the invention, in order to prevent rotational movements of the pad holder, at least two kinematic units form at least two parallelograms (and preferably no more than two parallelograms) which will constrain the position of the pad holder and force it to remain parallel to the pad holder located opposite it. It is unnecessary to form a third parallelogram at the third kinematic unit, because, as all rotations of the pad holder are already prevented by the first two parallelograms, the general structure of the drive device can be simplified by placing only a single connecting rod for this third kinematic unit, avoiding the formation of such a third parallelogram.

According to some embodiments of the invention, each kinematic unit comprises a motor which rotates a crank. One (in the absence of a parallelogram) or two (in the presence of a parallelogram) connecting rods are fixed to the crank via a double pivot connection. The rod or rods are also fixed by a double pivot connection to the pad holder. Two of the three kinematic units each form a parallelogram with two connecting rods, the third kinematic unit comprising only one connecting rod. Use of the connecting rod and crank system allows a simplified structure. The simplicity of the connecting rod and crank system arises in particular from the fact that applied forces can easily be absorbed through a connection with the frame, avoiding the application of forces to the motor shaft itself. The connecting rod and crank system simplifies the mechanical structure, but nevertheless requires management of the motors, which is a bit more complex in the software aspects. However, this complexity in the motor management software has no impact on the weight or size of the drive device, which can therefore be further miniaturized.

According to one possible variant of the embodiments of the invention, one or more kinematic units may not comprise a connecting rod and crank system, but be formed by a platform connected to a linear actuator, for example a worm gear motor, and to the connecting rods. This variant is possible, but remains more mechanically complex, however, and does not allow such advanced miniaturization as in the main embodiment based on the use of a connecting rod and crank system.

To solve the problem of simplifying the structure of the catheter robot, without simultaneously solving the problem involving precision through managing parasitic rotations of the pad holder, another object of the invention, in a somewhat degraded embodiment, can concern a drive module for an elongate flexible medical device of a catheter robot, comprising: at least two drive devices respectively carrying two pad holders located opposite one another and respectively intended to receive two pads which, as they approach each other, will grip the elongate flexible medical device in order to then drive it in translation and/or in rotation, each drive device being self-supporting and comprising three drive units which are independent of each other, driving the pad holder in translation respectively in the three orthogonal spatial directions, and each comprising their drive motor: a self-supporting drive device being a drive device in which the structure itself ensures that the pad holder is held in position without the presence of an additional support element, a drive unit that is independent of the other drive units being a drive unit which only supports its own weight without also supporting the weight of another drive unit, and in which at least two drive units have a structure which comprises: a drive crossmember, driven by the drive motor, having a longitudinal axis, a pad holder crossmember, rigidly connected to the pad holder and driven by the drive crossmember, a crank driven to rotate about its axis by the drive motor, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

According to preferred embodiments, the invention comprises one or more of the following features which can be used separately or in combinations applying some of them or in combinations applying all of them, for one or another of the aforementioned objects of the invention.

Preferably, the two connecting rods are parallel to each other.

The shape of the connecting rods which allow creating the deformable parallelogram kinematics is thus the simplest. But other shapes are conceivable for the connecting rods, for example curved connecting rods or segmented connecting rods having several segments, even if these other shapes for the connecting rods would be less practical.

Preferably, for at least one drive unit having a rotation-preventing structure: the rotation-preventing structure of the drive unit also comprises a crank driven to rotate around its axis by said drive motor, the drive crossmember having a longitudinal axis extending between its two pivoting points, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

The mechanical structure of the drive unit is thus further simplified, which further improves the miniaturization of the drive module, at the cost however of somewhat increasing the complexity of the software management of this drive module. But, overall, the benefit of miniaturization far outweighs the disadvantage of complexity in the software management.

Preferably, for at least two drive units having a rotation-preventing structure, for each of these two drive units: the rotation-preventing structure of the drive unit also comprises a crank driven to rotate about its axis by said drive motor, the drive crossmember having a longitudinal axis extending between its two pivoting points, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

The mechanical structure of the drive unit is thus further simplified, which further improves the miniaturization of the drive module, at the cost however somewhat increasing the complexity of the software management of this drive module. But, overall, the benefit of miniaturization far outweighs the disadvantage of complexity in the software management.

Preferably, only two drive units per drive device have a rotation-preventing structure.

Thus, as each structure is capable of preventing two parasitic rotations by using only two rotation-preventing structures, the three parasitic rotations are prevented, and the overall structure of the drive device remains simpler with only two rotation-preventing structures rather than three rotation-preventing structures.

Preferably, for the third drive unit not having a rotation-preventing structure, the structure of said drive unit comprises: a drive crossmember, driven by the drive motor, a pad holder crossmember, rigidly connected to the pad holder and driven by the drive crossmember, a single connecting rod respectively connected: by one of its ends to a pivoting point of the drive crossmember, and by its other end to a pivoting point of the pad holder crossmember.

Thus, as the three parasitic rotations are already prevented by the two rotation-preventing structures of two of the three drive units of each drive device, the structure of the third drive unit of this drive device can be simplified by not integrating any rotation-preventing structure, thereby further improving the miniaturization of the drive module.

Preferably, for said third drive unit not having a rotation-preventing structure: the structure of said drive unit also comprises a crank driven to rotate around its axis by said drive motor, the drive crossmember having a longitudinal axis, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

The structure of the third drive unit of this drive device can thus be further simplified, further improving the miniaturization of the drive module.

Preferably, for one drive unit or for several drive units or for all the drive units, said drive motor or motors are rotary motors driving the rotation of a crank rigidly connected to said drive crossmember.

The structure of the drive units is thus made even more compact.

Alternatively, for a drive unit or for several drive units or for all the drive units, said drive motor or motors are rotary motors driving the rotation of a worm screw so as to drive said drive crossmember in translation.

However, this alternative is less compact than the previous one.

Preferably, for each drive device: for each of the three drive units of said drive device: the drive unit drives the pad holder: along a main translational component in a main direction, said main direction being different for each of the three drive units, and along a parasitic translational component in another direction, said other direction being different for each of the three drive units; each of the three drive units of said drive device incorporates, in its main translational component in its main direction, a compensation for the parasitic translational component of one of the other drive units in this main direction.

The actions of the three drive units of said drive device are thus mutually balanced so that the pad holder receives overall, in each of the three spatial directions, the translation command required for the movement desired in this direction, as resulting in this direction from all the commands received from the three drive units.

Preferably, said pivoting points are hinges that can pivot with two degrees of freedom.

Other features and advantages of the invention will become apparent upon reading the following description of a preferred embodiment of the invention, given by way of example and with reference to the appended drawings.

6

Figure 1:
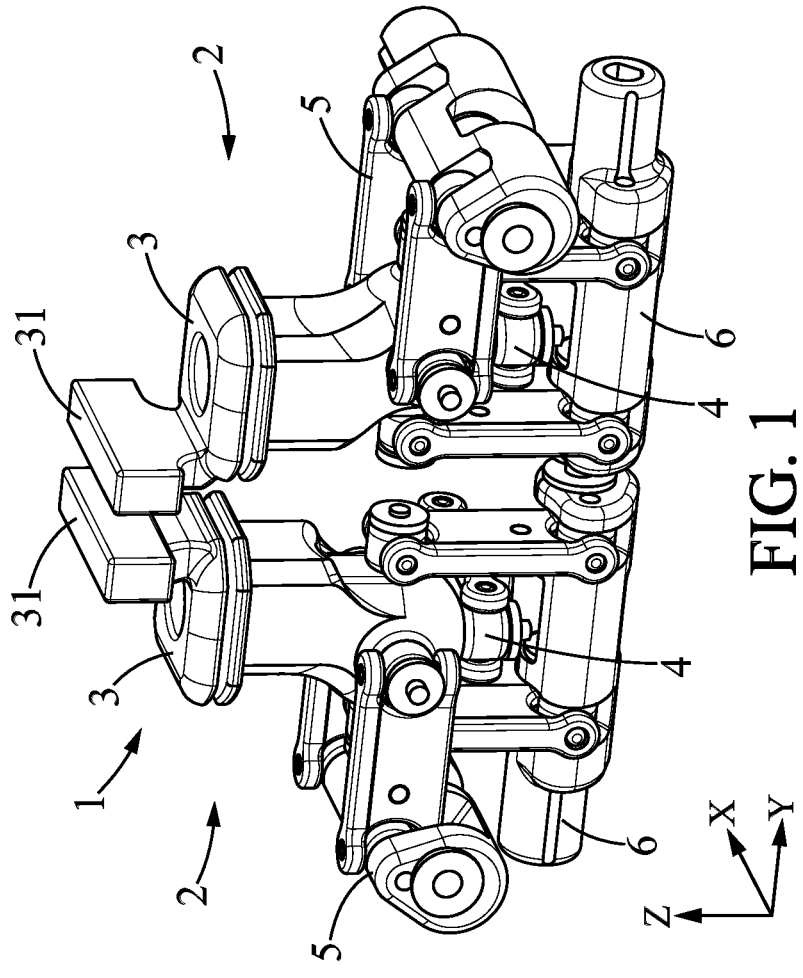
FIG. 1 schematically represents, in perspective view, an example of a drive module for an elongate flexible medical device which comprises two identical drive devices for pad holders, located opposite one another, according to one embodiment of the invention.
Figure 2:
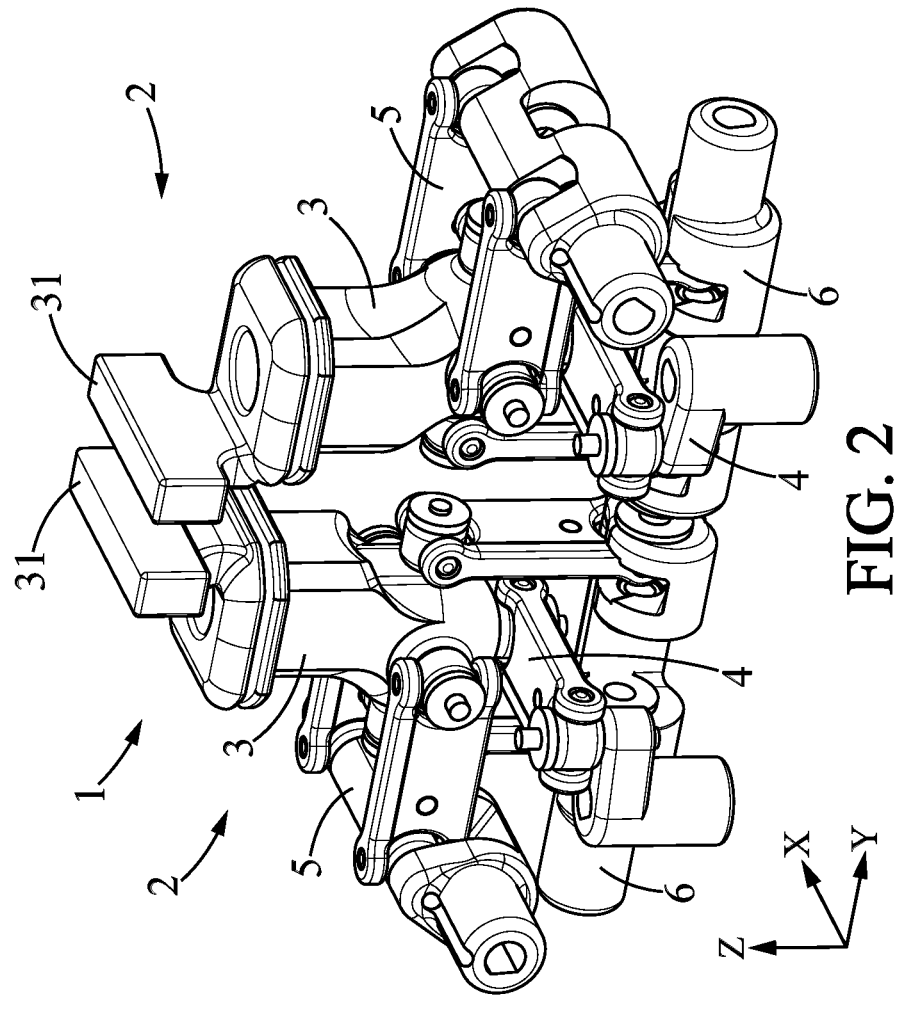
FIG. 2 schematically represents, in a perspective view opposite to the perspective in FIG. 1, the same example of a drive module for an elongate flexible medical device which comprises two identical drive devices for pad holders, located opposite one another, according to one embodiment of the invention.
Figure 4:
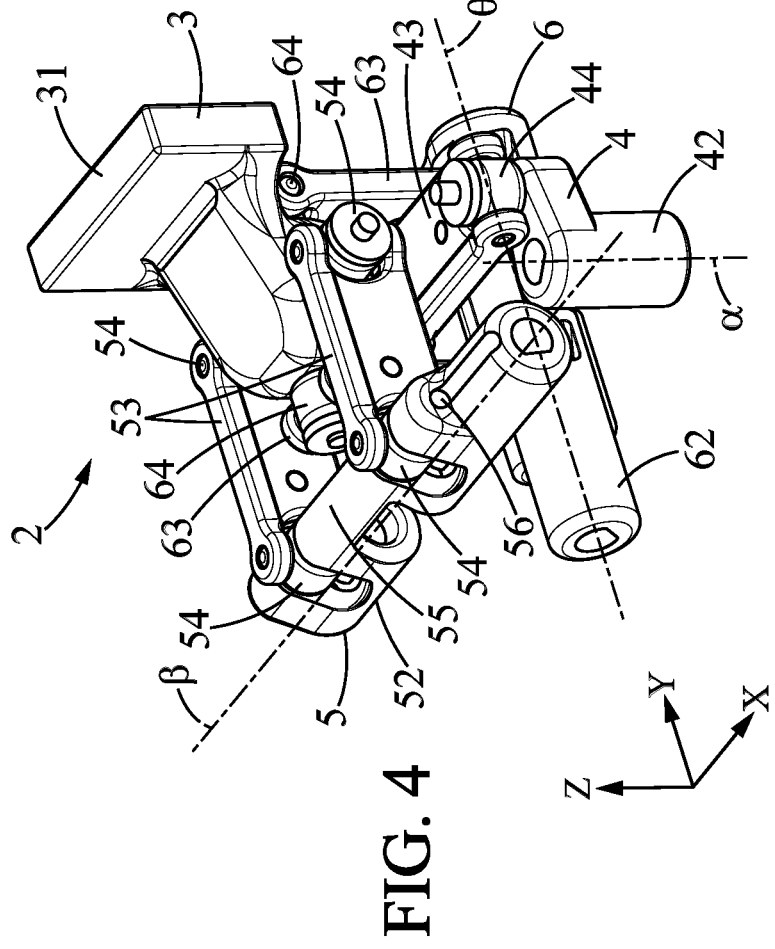

FIG. 4 schematically represents an example of a drive device of a drive module according to FIGS. 1 and 2, but not showing the motors of the various kinematic units of this drive device.

Figure 3:
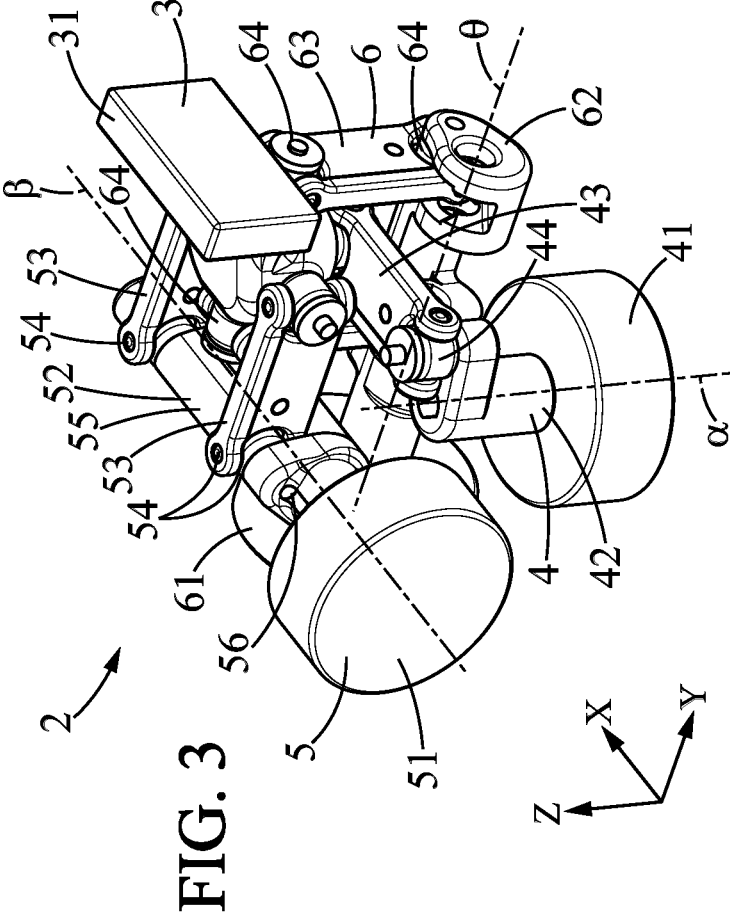
FIG. 3 schematically represents an example of a drive device of a drive module according to FIGS. 1 and 2, showing the motors of the various kinematic units of this drive device.
Figure 5:
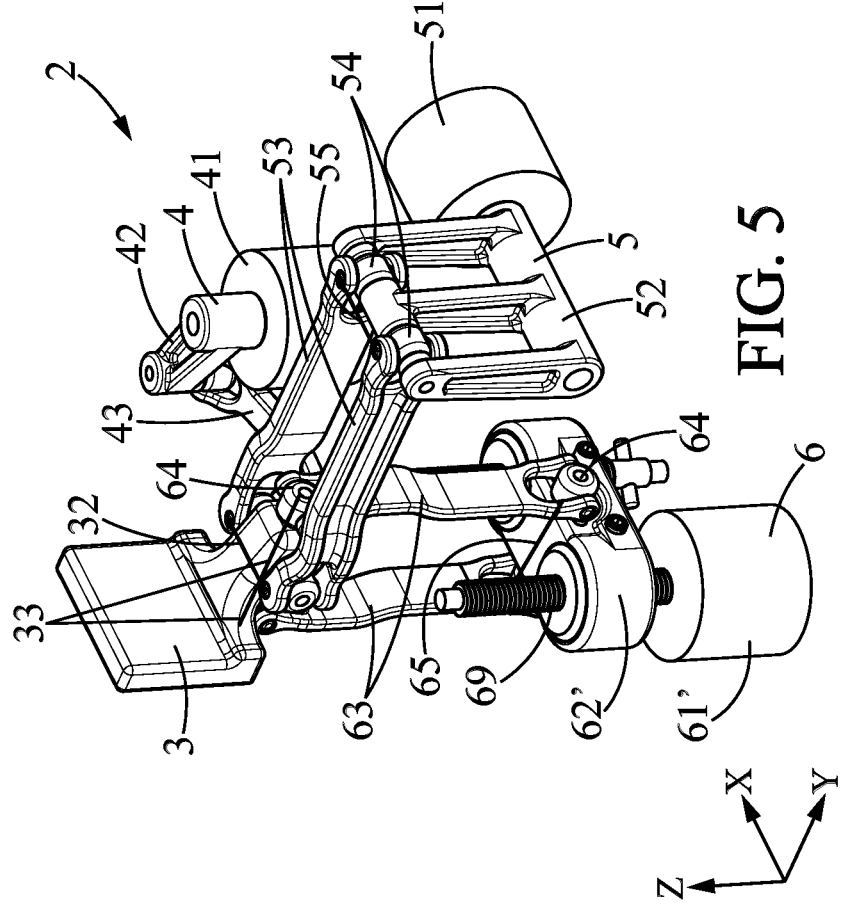

FIG. 5 schematically represents an example of a drive device of a drive module, showing the motors of the various kinematic units of this drive device, for one possible variant of FIG. 3, a variant in which a kinematic unit comprises a platform moved by a linear actuator instead of a connecting rod and crank system.

Figure 6:
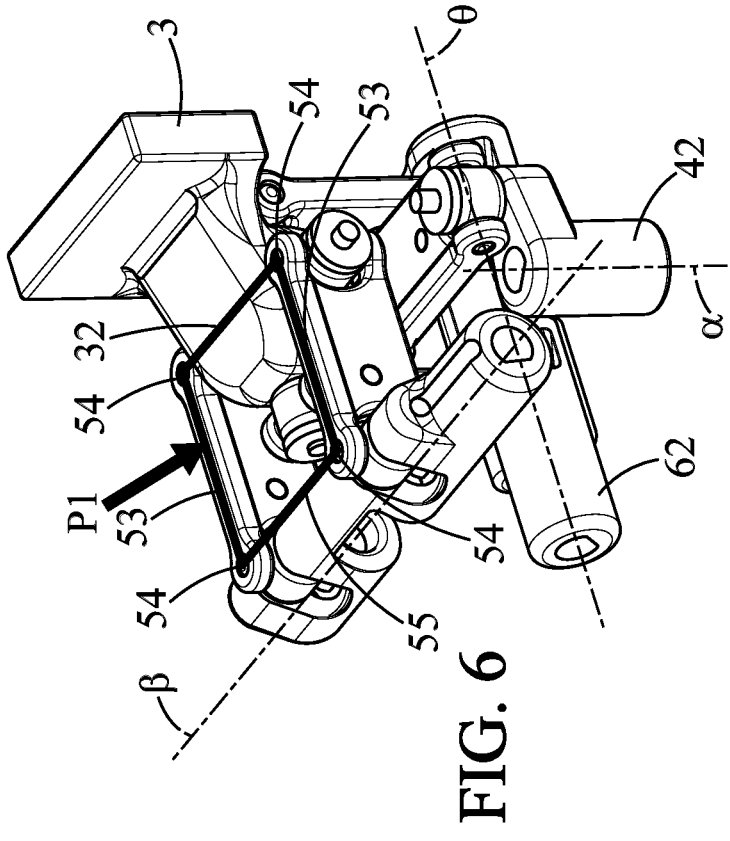

FIG. 6 schematically represents an example which highlights a first deformable parallelogram of the rotation-preventing structure of a first kinematic unit of the drive device according to FIG. 3.

Figure 7:
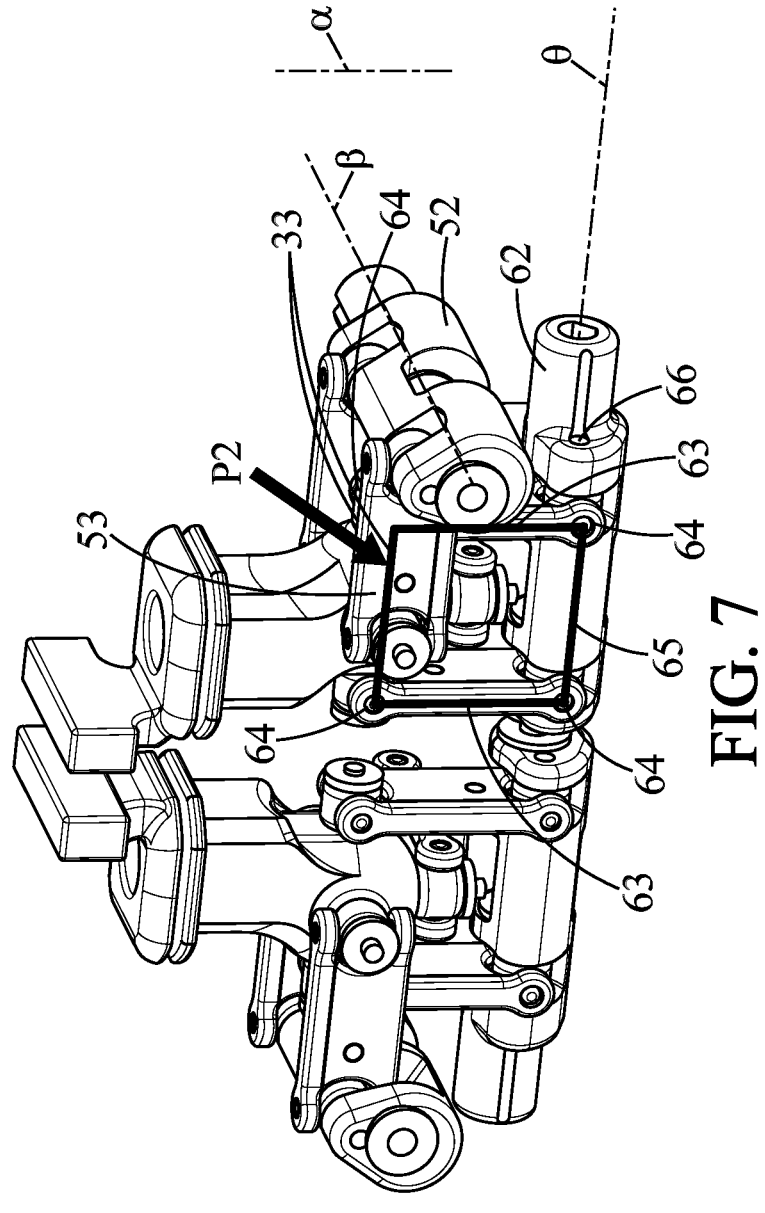

FIG. 7 schematically represents an example which highlights a second deformable parallelogram of the rotation-preventing structure of a second kinematic unit of the drive device according to FIGS. 1 and 2.

DETAILED DESCRIPTION OF EMBODIMENTS OF THE INVENTION

In the description of the figures which follows, the elongate flexible medical device may for example be a guide catheter or a catheter, for example of the balloon or stent type, or else a catheter guidewire.

FIG. 1 schematically represents, in a perspective view, an example of a drive module for an elongate flexible medical device which comprises two identical drive devices for pad holders, located opposite one another, according to one embodiment of the invention.

FIG. 2 schematically represents, in a perspective view opposite to the perspective of FIG. 1, the same example of a drive module for an elongate flexible medical device which comprises two identical drive devices for pad holders, located opposite one another, according to one embodiment of the invention.

Drive module 1 for an elongate flexible medical device comprises at least one pair of drive devices 2 for pad holders which are identical to each other and which are located opposite one another. Drive devices 2 of each pair are separated from each other by a space intended to receive the elongate flexible medical device which will be manipulated by drive module 1. Drive module 1 can perform a translation and/or a rotation of the elongate flexible medical device. Drive module 1 is controlled by a control unit 7 which will be described in more detail below, in connection with the operation of drive module 1 as described for FIGS. 3 and 4.

Each drive device 2 comprises a pad holder 3 which is a member which forms a manipulating finger of drive module 1. Pad holder 3 of each drive device 2 is intended to manipulate the elongate flexible medical device by cooperating with pad holder 3 of the other drive device 2 of the pair. The manipulation of the elongate flexible medical device by the pair of pad holders 3, in order to impart a translational, rotational, or combined translational and rotational movement to the flexible medical device, is described in patent application WO2015189531A2 (see in particular FIGS. 7a-7e and 8a-8e), incorporated herein by reference.

In order to ensure sterility of the medical device manipulated by pad holders 3, a single-use sterilized pad (not shown in the figures) is installed on each pad holder 3 and forms the interface between pad holder 3 and the elongate flexible medical device, this pad being replaced with each new use of drive module 1 by a new sterilized pad. The pad is installed on a manipulation portion 31 of pad holder 3 which protrudes from drive module 1.

In order to manipulate the elongate flexible medical device, pad holder 3 of each drive device 2 can be driven in translation, along each of the three orthogonal spatial axes x, y and z. In order to ensure proper manipulation of the elongate flexible medical device, pad holder 3 should not undergo any rotational movement, so manipulation portions 31 of pad holders 3 remain parallel to each other: this is in order to grip the elongate flexible medical device properly but without squeezing it too much.

Each drive device 2 comprises three kinematic units 4, 5 and 6, which are each intended to move pad holder 3 along one of the three orthogonal spatial axes x, y and z. Each drive device 2 therefore comprises a first kinematic unit 4 which moves pad holder 3 along the x axis, a second kinematic unit 5 which moves pad holder 3 along the y axis, and a third kinematic unit 6 which moves pad holder 3 along the z axis. In addition, the set of three kinematic units 4, 5 and 6 forms a self-supporting system which maintains pad holder 3 in the stationary position. Such a self-supporting system makes it possible to eliminate the presence of an additional device for holding pad holder 3, which simplifies drive module 1 while also reducing its bulk and its weight.

FIG. 3 schematically represents an example of a drive device of a drive module according to FIGS. 1 and 2, showing the motors of the various kinematic units of this drive device.

FIG. 4 schematically represents an example of a drive device of a drive module according to FIGS. 1 and 2, but not showing the motors of the various kinematic units of this drive device.

First kinematic unit 4 comprises a first motor 41 which rotates a first crank 42 about an axis of rotation α which is oriented along the z axis. A connecting rod 43 is fixed to crank 42 via a double pivot connection 44, the attachment between connecting rod 43 and crank 42, at double pivot connection 44, being offset from the axis of rotation α of crank 42 and of first motor 41. Connecting rod 43 is fixed at its other end to pad holder 3 via a double pivot connection 44 which is identical to the one establishing the connection between connecting rod 43 and crank 42. Double pivot connections 44 are connections which allow rotation about the z axis, and rotation about an axis perpendicular to the z axis. Rotation of first motor 41 thus causes a displacement of pad holder 3 which is primarily a translation along the x axis.

Second kinematic unit 5 comprises a second motor 51 which rotates a second crank 52 about an axis of rotation β which is oriented along the x axis. Two connecting rods 53 are fixed to crank 52, each of connecting rods 53 via a double pivot connection 54, the attachment, at double pivot connection 54, between each of connecting rods 53 and the crank 52 being offset from the axis of rotation β of crank 52 and of second motor 51. Connecting rods 53 are each fixed, at their other end, to pad holder 3 via a double pivot connection 54 identical to those establishing the connection with crank 52. Connecting rods 53 are parallel and are located one on either side of pad holder 3 so as to surround it. Connecting rods 53, axis 56 or crossmember 55 of crank 52, and pad holder 3 together form a parallelogram, which will be described in more detail in FIG. 6, the two connecting rods 53 forming two opposite sides and crank 52 and pad holder 3 forming the other two opposite sides. Crossmember 55 of crank 52 is the physical manifestation of this portion 55 of crank 52 which is located between the two double pivot connections 54.

Double pivot connections 54 are connections which allow rotation about the x axis, and rotation about an axis perpendicular to the x axis. Rotation of second motor 51 thus causes a displacement of pad holder 3 which is mainly a translation along the y axis.

Third kinematic unit 6 comprises a third motor 61 which rotates a third crank 62 about an axis of rotation θ which is oriented along the y axis. Two connecting rods 63 are fixed to crank 62, each of connecting rods 63 via a double pivot connection 64, the attachment, at double connection 64, between each of connecting rods 63 and the crank 62 being offset from the axis of rotation θ of crank 62 and of second motor 61. Connecting rods 63 are each fixed, at their other end, to pad holder 3 via a double pivot connection 64 identical to those establishing the connection with crank 62. Connecting rods 63 are parallel and are located one on either side of pad holder 3 so as to surround it. Connecting rods 63, crank 62, and pad holder 3 together form a parallelogram, which will be described in more detail in FIG. 7, the two connecting rods 63 forming two opposite sides and crank 62 and pad holder 3 forming the other two opposite sides. Double pivot connections 64 are connections which allow rotation about the y axis, and rotation about an axis perpendicular to the y axis. Rotation of second motor 61 thus causes a displacement of pad holder 3 which is mainly a translation along the z axis.

In one embodiment, first motor 41, second motor 51, and third motor 61 are rotary motors, which makes it possible to simplify drive device 2. According to another possible variant, cranks 42, 52 and 62 can be rotated by a linear motor for which the connection with each of cranks 42, 52 and 62 is offset from the axis of rotation of the crank in the same way as the connecting rods in FIGS. 3 and 4.

The connecting rod and crank structure of kinematic units 4, 5 and 6 also makes it possible to simplify the absorption of forces without stressing the motors. One simple solution is to have a pivot connection for each connecting rod, which connects this connecting rod to the frame, the pivot connection being located at the end of the crank which is opposite to the end of the connecting rod which is connected to the motor.

In the embodiment shown in FIGS. 1 to 4, actuation of a kinematic unit does not move pad holder 3 in translation along only a single axis, the movement of pad holder 3 being in fact a translation which comprises a main component along one axis and a secondary component along another axis. This secondary component, much less significant than the main component, is a parasitic component which will be compensated for. For example, actuation of second kinematic unit 5 with rotation of motor 51 causes a translational movement of pad holder 3 with a main component along the y axis and a secondary component along the z axis.

In order to compensate for this secondary component, drive module 1 comprises a control unit 7 which controls the operation of kinematic units 4, 5 and 6, the control unit 7 activating kinematic units 4, 5 and 6 so that the movement of pad holder 3 corresponds to the user's command. For example, if the user commands a pure rotational movement of the catheter, meaning a pure translational movement along the z axis of pad holder 3, control unit 7 simultaneously controls the activation of the three kinematic units 4, 5 and 6. Third kinematic unit 6 is activated to impart a translational movement to the pad holder with a main component along the z axis and a secondary component along the x axis. In order to compensate for the secondary x-axis component, first kinematic unit 4 is activated in order to keep pad holder 3 fixed along the x axis, the activation of first kinematic unit 4 creating a secondary y-axis component, however. To compensate for the secondary y-axis component, second kinematic unit 5 is also activated in order to keep pad holder 3 fixed along the y axis, activation of second kinematic unit 5 however creating a secondary z-axis component which is taken into account by control unit 7 in its instructions to kinematic units 4, 5 and 6. The three kinematic units 4, 5 and 6 are activated simultaneously in order to generate all the main components desired by the user and to compensate for all the parasitic secondary components not desired by the user.

In the embodiment represented in FIGS. 1 to 4, the mechanical structure of drive module 1 is simplified, which however complicates the algorithm for managing the activation of kinematic units 4, 5 and 6, depending on the movement requested by the user and implemented by control unit 7.

FIG. 5 schematically represents an example of a drive device of a drive module, showing the motors of the various kinematic units of this drive device in one possible variant of FIG. 3, a variant where a kinematic unit comprises a platform moved by a linear actuator instead of a connecting rod and crank system.

According to a possible variant which is illustrated in FIG. 5, one or more kinematic units 4, 5 and 6 may not be formed by a connecting rod and crank system. Drive device 2 has a third kinematic unit 6 whose function is to move pad holder 3 along the z axis and which comprises a platform 62' which is driven in translation along the z axis by a linear actuator 61'. Rotation of platform 62' is prevented about any of the three axes, and translation is also prevented along the x axis and y axis. Similarly to crank 62 of the embodiment of FIGS. 1 to 4, platform 62' is connected to two connecting rods 63 via double pivot connections 64. Connecting rods 63 are also connected to pad holder 3 via double pivot connections 64. Double pivot connections 64 are connections which allow rotation about the y axis, and rotation about an axis perpendicular to the y axis.

In FIG. 5, a first parallelogram is formed by two connecting rods 63, platform 62', and pad holder 3, in fact more precisely by two connecting rods 63, drive crossmember 65 of platform 62', and pad holder 3 crossmember 33. This first parallelogram prevents rotational movements of pad holder 3 around the x and z axes. Crossmember 65 of crank 62 is the physical manifestation of this portion 65 of crank 62 which is located between the two double pivot connections 64. In a manner similar to the embodiment shown in FIGS. 1 to 4, the second parallelogram is formed by connecting rods 53, crank 52, and pad holder 3, in fact more precisely by two connecting rods 53, drive crossmember 55 of crank 52, and pad holder 3 crossmember 32.

Actuator 61' is a worm gear motor 69 in the variant illustrated in FIG. 5, although other types of linear actuators may be used instead.

The variant illustrated in FIG. 5 does not offer the same mechanical simplicity as the variant of FIGS. 1 to 4, particularly concerning the positioning of a connection with platform 62' in order to absorb forces without stressing actuator 61'.

FIG. 6 schematically represents an example which highlights a first deformable parallelogram of the rotation-preventing structure of a first kinematic unit of the drive device according to FIG. 3.

Connecting rods 53, axis 56 or crossmember 55 of crank 52, and pad holder 3 crossmember 32 together form a first parallelogram P1, the two connecting rods 53 forming two opposite sides and axis 56 or crossmember 55 of crank 52 and pad holder 3 crossmember 32 forming the other two opposite sides. The four sides of first parallelogram P1 can move relative to each other by pivoting around double connections 54, while always keeping the two rods 53 parallel to each other and the axis 56 or crossmember 55 of crank 52 and the pad holder 3 crossmember 32 parallel to each other. First parallelogram P1 can therefore be deformed by pivoting its four sides around its four vertices which are the four double connections 54, but still remains a parallelogram.

First parallelogram P1 was chosen in connection with axis of rotation β, but it could have been chosen in connection with either axis of rotation θ or axis of rotation α.

FIG. 7 schematically represents an example which highlights a second deformable parallelogram of the rotation-preventing structure of a second kinematic unit of the drive device according to FIGS. 1 and 2.

Connecting rods 63, axis 66 or crossmember 65 of crank 52, and pad holder 3 crossmember 33 together form a second parallelogram P2, the two connecting rods 63 forming two opposite sides and the axis 66 or crossmember 65 of crank 62 and the pad holder 3 crossmember 33 forming the other two opposite sides. The four sides of second parallelogram P2 can move relative to each other by pivoting around double connections 64, while always keeping the two connecting rods 63 parallel to each other and axis 66 or crossmember 65 of crank 62 and pad holder 3 crossmember 33 parallel to each other. Second parallelogram P2 can therefore be deformed by pivoting its four sides around its four vertices which are the four double connections 64, but still remains a parallelogram.

Second parallelogram P2 was chosen in connection with axis of rotation θ, but it could have been chosen in connection with axis of rotation β or axis of rotation α.

The double-parallelogram structure of drive device 2, having parallelograms P1 and P2 respectively described in more detail in FIGS. 6 and 7, is a structurally simple solution which makes it possible to prevent all rotational movements of pad holder 3, while allowing all translational movements of said pad holder 3. Indeed, each parallelogram, P1 or P2, prevents rotation about two axes of rotation of pad holder 3, rotation about the three axes of rotation being prevented by adding the two parallelograms.

First parallelogram P1, which is formed by connecting rods 53, crank 52, and pad holder 3 crossmember 32, prevents rotations of said pad holder 3 along the y and z axes. Pad holder 3 crossmember 32 is only a physical manifestation of a portion of pad holder 3 connecting the two double pivot connections 54. Indeed, pad holder 3 is kept parallel to crank 52, and because crank 52 is only movable in rotation around the β axis (and therefore the x axis), rotational movements of pad holder 3 around the y and z axes are prevented.

Second parallelogram P2, which is formed by connecting rods 63, crank 63, and pad holder 3 crossmember 33, prevents rotations of said pad holder 3 along the x and z axes. Pad holder 3 crossmember 33 is only a physical manifestation of a portion of pad holder 3 connecting the two double pivot connections 64. Indeed, pad holder 3 is kept parallel to crank 62, and because crank 62 is only movable in rotation around the θ axis (and therefore the y axis), rotational movements of pad holder 3 around the x and z axes are prevented. For visibility in FIG. 7, second parallelogram P2 is shown in front of connecting rod 53 of the second kinematic unit, whereas in reality it is behind connecting rod 53, since in fact the four vertices of second parallelogram P2 are the four double connections 64.

The structure does not include a third parallelogram, because the use of a single connecting rod 43 at axis of rotation α makes it possible to simplify the structure: rotation about the three axes of rotation x, y and z is already prevented by the two parallelograms P1 and P2.

Of course, the invention is not limited to the examples and to the embodiment described and represented, but is capable of numerous variants accessible to those skilled in the art.

The invention claimed is:

1. Drive module for an elongate flexible medical device of a catheter robot, comprising:

at least two drive devices respectively carrying two pad holders located opposite one another and respectively intended to receive two pads which, as the two pads approach each other, will grip the elongate flexible medical device in order to then drive the elongate flexible medical device in translation and/or in rotation, each drive device being self-supporting and comprising three drive units which are independent of each other, driving the pad holder in translation respectively in the three orthogonal spatial directions, which each comprise their drive motor, and at least two of said three drive units have a rotation-preventing structure preventing rotational movements of the pad holder:

wherein each said self-supporting drive device is a drive device in which the drive device's own structure ensures that the pad holder is held in position without the presence of an additional support element, wherein each said drive unit that is independent of the other drive units is a drive unit which only supports the drive unit that is independent of the other drive units' own weight without also supporting the weight of another of said drive units, said rotation-preventing structure comprising:

a drive crossmember, driven by its respective drive motor, a pad holder crossmember, rigidly connected to the pad holder and driven by the drive crossmember, two connecting rods respectively connected:

by one of their ends to two pivoting points of the drive crossmember which are set apart from each other, by the other of their ends to two pivoting points of the pad holder crossmember which are set apart from each other, the drive crossmember, the pad holder crossmember, and the two connecting rods together forming a parallelogram that is deformable at the parallelogram's four vertices which are said four pivoting points.

2. Drive module according to claim 1, wherein the two connecting rods are parallel to each other.

3. The drive module according to claim 2, wherein, for at least one drive unit having a rotation-preventing structure:

the rotation-preventing structure of said at least one drive unit also comprises a crank driven to rotate around the crank's axis by said drive motor of said at least one drive unit, the drive crossmember having a longitudinal axis extending between two pivoting points of the drive crossmember, said axis of rotation of the crank being k and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

4. The drive module according to claim 2, wherein, for one drive unit or for several drive units or for all the drive units, said drive motor or motors are rotary motors driving the rotation of a crank rigidly connected to said drive crossmember.

5. The drive module according to claim 2, wherein, for one drive unit or for several drive units or for all the drive units, said drive motor or motors are rotary motors driving the rotation of a worm screw so as to drive said drive crossmember in translation.

6. Drive module according to claim 1, wherein, for at least one drive unit having a rotation-preventing structure:

the rotation-preventing structure of said at least one drive unit also comprises a crank driven to rotate around the crank's axis by said drive motor, the drive crossmember having a longitudinal axis extending between two pivoting points of the drive crossmember, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

7. The drive module according to claim 6, wherein, for one drive unit or for several drive units or for all the drive units, said drive motor or motors are rotary motors driving the rotation of a crank rigidly connected to said drive crossmember.

8. The drive module according to claim 6, wherein, for one drive unit or for several drive units or for all the drive units, said drive motor or motors are rotary motors driving the rotation of a worm screw so as to drive said drive crossmember in translation.

9. Drive module according to claim 6, wherein, for at least two drive units having a rotation-preventing structure, for each of these two drive units:

the rotation-preventing structure of the drive unit also comprises a crank driven to rotate around the crank's axis by said drive motor, the drive crossmember having a longitudinal axis extending between two pivoting points of the drive crossmember, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

10. Drive module according to claim 9, wherein only two drive units per drive device have a rotation-preventing structure.

11. The drive module according to claim 10, wherein, for one drive unit or for several drive units or for all the drive units, said drive motor or motors are rotary motors driving the rotation of a crank rigidly connected to said drive crossmember.

12. Drive module according to claim 10, wherein, for the third drive unit not having a rotation-preventing structure, the structure of said third drive unit comprises:

a drive crossmember, driven by the drive motor of the third drive unit, a pad holder crossmember, rigidly connected to the pad holder and driven by the drive crossmember, a single connecting rod respectively connected:

by one of the single connecting rod's ends to a pivoting point of the drive crossmember, by the single connecting rod's other end to a pivoting point of the pad holder crossmember.

13. The drive module according to claim 12, wherein, for one drive unit or for several drive units or for all the drive units, said drive motor or motors are rotary motors driving the rotation of a crank rigidly connected to said drive crossmember.

14. Drive module according to claim 12, wherein, for said third drive unit not having a rotation-preventing structure:

the structure of said third drive unit also comprises a crank driven to rotate around the crank's axis by said drive motor of said third drive unit, the drive crossmember having a longitudinal axis, said axis of rotation of the crank being and remaining parallel to said longitudinal axis of the drive crossmember, the inter-axis gap, meaning the gap between said axis of rotation of the crank and said longitudinal axis of the drive crossmember, being and remaining constant, such that rotation of the crank causes rotation of said longitudinal axis of the drive crossmember.

15. The drive module according to claim 14, wherein, for one drive unit or for several drive units or for all the drive units, said drive motor or motors are rotary motors driving the rotation of a crank rigidly connected to said drive crossmember.

16. The drive module according to claim 9, wherein, for one drive unit or for several drive units or for all the drive units, said drive motor or motors are rotary motors driving the rotation of a crank rigidly connected to said drive crossmember.

17. The drive module according to claim 1, wherein, for one drive unit or for several drive units or for all the drive units, said drive motor or motors are rotary motors driving the rotation of a crank rigidly connected to said drive crossmember.

18. The drive module according to claim 1, wherein, for one drive unit or for several drive units or for all the drive units, said drive motor or motors are rotary motors driving the rotation of a worm screw so as to drive said drive crossmember in translation.

19. The drive module according to claim 1, wherein, for each drive device:

for each of the three drive units of said drive device:

the drive unit drives the pad holder:

along a main translational component in a main direction, said main direction being different for each of the three drive units, and along a parasitic translational component in another direction, said other direction being different for each of the three drive units, each of the three drive units of said drive device incorporates, in the drive unit's main translational component along its main direction, a compensation for the parasitic translational component of one of the other drive units in this main direction.

20. The drive module according to claim 1, wherein said pivoting points are hinges that can pivot with two degrees of freedom.

* * * * *